US008704191B2

(12) United States Patent
Yu et al.

(10) Patent No.: US 8,704,191 B2
(45) Date of Patent: Apr. 22, 2014

(54) FILM BULK ACOUSTIC WAVE RESONATOR-BASED HIGH ENERGY RADIATION DETECTORS AND METHODS USING THE SAME

(75) Inventors: Hongyu Yu, Tempe, AZ (US); Jonathon Keith Oiler, Scottsdale, AZ (US); Hugh James Barnaby, Tempe, AZ (US)

(73) Assignee: Arizona Board of Regents, a Body Corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 106 days.

(21) Appl. No.: 13/513,287

(22) PCT Filed: Jan. 20, 2011

(86) PCT No.: PCT/US2011/021814
§ 371 (c)(1),
(2), (4) Date: Sep. 4, 2012

(87) PCT Pub. No.: WO2011/142845
PCT Pub. Date: Nov. 17, 2011

(65) Prior Publication Data
US 2012/0326050 A1  Dec. 27, 2012

Related U.S. Application Data

(60) Provisional application No. 61/296,707, filed on Jan. 20, 2010.

(51) Int. Cl.
*G01T 1/16* (2006.01)
*G01N 29/036* (2006.01)
*G01T 1/161* (2006.01)

(52) U.S. Cl.
CPC ............... *G01T 1/16* (2013.01); *G01N 29/036* (2013.01); *G01T 1/1606* (2013.01); *G01T 1/161* (2013.01)
USPC ........................................................ 250/395

(58) Field of Classification Search
CPC . H03H 9/0571; H03H 9/1007; G01N 29/022; G01N 2291/0256; G01N 29/036; G01T 1/1606
USPC .......................................................... 250/395
See application file for complete search history.

(56) References Cited

U.S. PATENT DOCUMENTS

2001/0038255 A1*  11/2001  Wadaka et al. ............ 310/313 R
2002/0008443 A1    1/2002  Yamada et al.
(Continued)

FOREIGN PATENT DOCUMENTS

EP          0771070          5/1997

OTHER PUBLICATIONS

Stanic et al. (2005). "Radiation monitoring in Mrad range using radiation-sensing field effect transistors." Nuc Inst Meth in Phys Res 545: 252-260.

(Continued)

*Primary Examiner* — Marcus Taningco
(74) *Attorney, Agent, or Firm* — McDonnell Boehnen Hulbert & Berghoff LLP

(57) ABSTRACT

The present invention relates generally to the detection of high energy radiation. The present invention relates more particularly to the film bulk acoustic wave resonator-based devices, and their use in the detection of high energy radiation. One aspect of the invention is a method for detecting high energy radiation, the method comprising providing a film bulk acoustic wave resonator having a zinc oxide piezoelectric layer in substantial contact with a dielectric layer; exposing the film bulk acoustic wave resonator to the high energy radiation; determining the resonant frequency of the film bulk acoustic wave resonator; and determining the dose of high energy radiation using the resonant frequency of the film bulk acoustic wave resonator.

27 Claims, 7 Drawing Sheets

(56) References Cited

U.S. PATENT DOCUMENTS

2004/0212458 A1    10/2004    Lee
2005/0093397 A1    5/2005    Yamada et al.

OTHER PUBLICATIONS

Jones et al. (2006). "Detection of shielded nuclear material in a cargo container." Nuc Inst and Methods in Phys Res A 562: 1085-1088.

Iyudin (2003). "Study of global galactic distribution of classical novae by their gamma-ray line emission at 1.275 MeV." Nuc Phys A 718: 413-415.

Black et al. (2005). "An analysis of an implantable dosimeter system for external beam therapy." Int J Rad Onc Bio Phys 63: 290-300.

Takeyasu et al. (2006). "Concentrations and their ratio of 222Rn decay products in rainwater measured by gamma-ray spectrometry using a low-background GE detector." J Environ Radioact 88: 74-89.

Beyer et al. (2008). "An implantable MOSFET dosimeter for the measurement of radiation dose in tissue during cancer therapy." IEEE Sensors Journal 8: 38-51.

Son et al. (2006). "A micromachined electret-based transponder for in situ radiation measurement." IEEE Elec Dev Let 27: 884-886.

Son et al. (2008). "A wireless implantable passive microdosimeter for radiation oncology." IEEE Trans Biomed Eng 55: 1772-1775.

Ueda et al. (2008). "Development of an X-band filter using air-gap-type film bulk acoustic resonators." Jpn J Appl Phys 47: 4007-4010.

Zhang et al. (2005). "Micromachined acoustic resonant mass sensor." J Microelectromech Sys 14: 699-706.

Qiu et al. (2003). "Film bulk acoustic-wave resonator based ultraviolet sensor." App Phys Let 94: 151917.

Larson III et al. (2000). "Modified Butterworth-Van Dyke circuit for FBAR resonators and automated measurement system." IEEE Ultrasonics Symposium 1: 863-868.

Oldham (1984). "Analysis of damage in MOS devices in several radiation environments." IEEE Trans Nucl Sci NS-31: 1236-1241.

Esqueda et al. (2009). "Modeling the radiation response of fully-depleted SOI n-channels MOSFETs." IEEE Trans Nucl Sci 56: 2247-2250.

Barnaby et al. (2009). "Modeling ionizing radiation effects in solid state materials and CMOS devices." IEEE Trans Circ Sys 56: 1870-1883.

Rashkeev et al. (2002). "Physical model for enhanced interface-trap formation at low dose rates." IEEE Trans Nucl Sci 49: 2650-2655.

Oiler et al. (2010). "Film Bulk Acoustic-Wave Resonator Based Radiation Sensor." Proc. 5th IEEE Int Conf Nano/Micro Eng Mol Sys, Xiamen, China.

International Search Report of International Patent Application No. PCT/US2011/021814, filed Jan. 20, 2011, mailed Nov. 21, 2011.

Written Opinion of International Patent Application No. PCT/US2011/021814, filed Jan. 20, 2011, mailed Nov. 21, 2011.

\* cited by examiner

US 8,704,191 B2

FILM BULK ACOUSTIC WAVE RESONATOR-BASED HIGH ENERGY RADIATION DETECTORS AND METHODS USING THE SAME

CROSS-REFERENCE TO RELATED APPLICATIONS

This application claims the priority of U.S. Provisional Patent Application Ser. No. 61/296,707, filed Jan. 20, 2010, which is hereby incorporated herein by reference in its entirety.

BACKGROUND OF THE INVENTION

1. Field of the Invention

The present invention relates generally to the detection of high energy radiation. The present invention relates more particularly to the film bulk acoustic wave resonator-based devices, and their use in the detection of high energy radiation.

2. Technical Background

Ionizing radiation sensing has a wide range of applications. High dose radiation measurements are important for understanding the degradation of silicon-based electronics in large high energy physics experiments [1]. Low dose sensing is essential in nuclear materials detection and security, where the sources may be partially shielded [2]. Measuring the flux and direction of high energy radiation with space-based detectors is important in the field of astronomy [3]. Determining the precise location and amount of radiation incident on a tumor or other tissues is critical in radiation therapies used in cancer treatment [4].

There are a number of different types of sensors used in the detection of radiation. For very high precision, gamma ray spectrometry can be used [5] but these devices are often extremely expensive and large in size. Lithium fluoride or calcium fluoride thermoluminescent dosimeters (TLDs) are often used in biomedical applications [6]. In order to determine the received dose after exposure, the TLD is heated and the amount of light emitted is measured using a spectrometer. These dosimeters are relatively inexpensive but require significant post-processing to determine the absorbed dose.

In biomedical applications, miniature devices are especially important because they are less invasive and can be placed closer to the target location and thus give more accurate results. Solid-state MOSFET dosimeters (RADFETs) are active devices that have been developed over the past decade and have high sensitivities, but when used in wireless communications require a large inductor which limits the ability to miniaturize the device [7]. Existing MicroElectroMechanical Systems (MEMS) research employs electret-based variable capacitors for measuring radiation, where the electric field generated by the electret collects charge from ionizing radiation in an air gap, reducing the surface charge density which varies the force on the movable plate [8-9]. This capacitor also needs to operate in conjunction with an inductor and by monitoring the resonant frequency of the circuit the signal dosage is determined Therefore, the sensor size due to large inductor, with its low quality factor, limits the ability of integration, and sensitivity may also be affected by ions released into the air gap during fabrication (wall effect).

SUMMARY OF THE INVENTION

According to one aspect of the invention, a method for detecting high energy radiation includes:
- providing a film bulk acoustic wave resonator having a zinc oxide piezoelectric layer in substantial contact with a dielectric layer;
- exposing the film bulk acoustic wave resonator to the high energy radiation;
- determining the resonant frequency of the film bulk acoustic wave resonator; and
- determining the dose of high energy radiation using the resonant frequency of the film bulk acoustic wave resonator.

According to another aspect of the invention, a high energy radiation detector comprises a film bulk acoustic wave resonator having a zinc oxide piezoelectric layer in substantial contact with a dielectric layer; and a system adapted to determine a dose of high energy radiation using a resonant frequency measured by the resonant frequency measuring circuit.

Various embodiments according to these aspects of the invention are described below.

The sensors and methods of the present invention can be used as integrating sensors for radiation, i.e., the frequency shift changes continuously as more total radiation impinges on the sensor.

In certain embodiments, the zinc oxide piezoelectric layer and the dielectric layer are disposed between a first electrode layer and a second electrode layer.

In one embodiment, the film bulk acoustic wave resonator includes:
- a dielectric diaphragm layer (e.g., 0.05-1.5 µm thick) suspended above a void space, the dielectric diaphragm layer having a first side and a second side;
- a zinc oxide piezoelectric layer (e.g., 0.2-4.0 µm thick) disposed on the first side of the dielectric diaphragm layer;
- a first electrode layer (e.g., 0.05-1.0 µm thick) disposed on the zinc oxide piezoelectric layer;
- a second electrode layer (e.g., 0.05-0.5 µm thick) disposed on the second side of the dielectric diaphragm layer; and
- a resonant frequency measuring circuit operatively coupled to the first electrode layer and the second electrode layer.

In another embodiment, the film bulk acoustic wave resonator includes
- a diaphragm layer suspended above a void space, the diaphragm layer having a first side and a second side;
- a first electrode layer (e.g., 0.05-1.0 µm thick);
- a second electrode layer (e.g., 0.05-0.5 µm thick);
- a zinc oxide piezoelectric layer (e.g., 0.2-4.0 µm thick) and a dielectric layer (e.g., PECVD-deposited silicon nitride, for example, 0.05-1.5 µm thick) disposed in substantial contact with one another and disposed between the first electrode layer and the second electrode layer;
- a resonant frequency measuring circuit operatively coupled to the first electrode layer and the second electrode layer.

The layer of dielectric material can be formed from a variety of substances, such as silicon nitride, silicon oxide, or polymer. The layer of dielectric material can be deposited, for example, using a chemical process (e.g., plasma-enhanced chemical vapor deposition) at process temperatures less than about 500° C. (e.g., at about 300° C.), so as to produce a substantial number of defects in the dielectric layer. These defects become the sites used for charge trapping, which can result in stronger radiation sensitivity. Because the charge trapping occurs in the dielectric layer, the diaphragm can be made from a higher quality material, thereby increasing the quality factor of the device. In certain embodiments, the concentration of defects in the dielectric layer is in the range of $1\times10^{11}/cm^2$ to b $1\times10^{14}/cm^2$ The diaphragm layer can be made of a variety of substances. In certain embodiments, the diaphragm layer is made from a dielectric material. For example, in one embodiment, the diaphragm layer is made from silicon nitride. In other embodiments, the diaphragm layer can be made from silicon dioxide. In such embodiments, the dielectric diaphragm layer can be disposed in substantial contact with the zinc oxide piezoelectric layer, so that a separate dielectric layer need not be provided. The person of skill in the art can select other substances for use in the diaphragm layer, and a separate dielectric layer can be provided (e.g., as described below with respect to FIG. 1).

The electrode layers can be made of a variety of substances. For example, in certain embodiments, the first and second electrode layers are made from gold (optionally deposited on a thin layer of chromium to enhance adhesion). Of course, other materials can be used for the electrodes, such as molybdenum, platinum, or aluminum.

The various elements can be formed in a variety of shapes and sizes. As the person of skill in the art will recognize, the sensitivity and resonant frequency of the device can depend on the shapes and sizes of the various elements. For example, in one embodiment, the zinc oxide piezoelectric layer can have a surface area in the range of 0.0025 $mm^2$ to 0.2 $mm^2$ In certain embodiments, the shapes, thicknesses and sizes of the various elements are selected to yield a resonant frequency in the range of 0.2 GHz to 10 GHz.

The zinc oxide layer can be, for example, substantially crystalline. In one embodiment, the zinc oxide layer is substantially crystalline with its wurzite C axis substantially perpendicular to its opposed surfaces.

The measurement can be performed at a wide variety of temperatures. It may be desirable to include a temperature sensor (e.g., a thermistor) near the FBAR, in order to allow temperature calibration.

In certain embodiments, the high energy radiation has an energy in the range of 1 keV to 100 MeV. For example, in one embodiment, the high energy radiation has an energy in the range of 0.1 MeV to 10 MeV. The high energy radiation can be, for example, gamma radiation.

In certain embodiments, the high energy radiation is from a $^{60}$Co source.

In certain embodiments, the high energy radiation is from a radiation treatment for cancer. The sensors and methods described herein can be used to detect the total dose at a point, for example, on the patient's body, either at the location desired to be irradiated, or at some other location to determine undesired exposure. For example, in certain embodiments, the small size of an FBAR device will allow it to be placed near critical organs, where it can monitor the amount of stray radiation those organs receive during radiotherapy.

In certain embodiments, the high energy radiation is from a suspected nuclear weapon. The sensors and methods described herein can be used in national security systems to detect the energy radiating from a hidden nuclear device.

In certain embodiments, the high energy radiation is from outer space. The sensors and methods described herein can be used to detect radiation in astronomical applications.

In certain embodiments, the total dose detected by the sensor is in the range of 20 rad to 1000 krad.

The devices and methods of the present invention can be adapted for use with telemetry methods to allow remote detection of high energy radiation. Telemetry is well-known to the person of skill in the art, and is described, for example, in Russell G. DeAnna, "Wireless Telemetry for Gas-Turbine Applications," NASA/TM-2000-209815, ARL-MR-74, March 2000, available at http://www.dlnet.vt.edu/repository/previewRepository/AE000000/AE005000/AE0050 05/DISK1/DLNET-12-06-2002-0112/resources/TM-2000-209815.pdf, which is hereby incorporated by reference in its entirety.

BRIEF DESCRIPTION OF THE DRAWINGS

The accompanying drawings are not necessarily to scale, and sizes of various elements can be distorted for clarity.

DETAILED DESCRIPTION OF THE INVENTION

The present disclosure relates to the sensing of high energy radiation (e.g., gamma radiation) using a zinc oxide based Film Bulk Acoustic-wave Resonator (FBAR). Film bulk acoustic-wave resonators have been well developed for filters [10], high sensitivity mass sensors [11], and ultraviolet sensors [12] owing to their high quality factor at operation frequencies of 0.2 to 10 GHz. The exemplary devices disclosed herein are MEMS-based film bulk acoustic-wave resonators (FBARs) with a high quality factor, extremely small size and the ability to be readout wirelessly. The sensors of the present invention can have a much smaller size than other radiation sensors because they do not require a large inductor coil. Moreover, with a resonant frequency of ~2 GHz and a high quality factor, certain devices of the invention can be extremely suitable for wireless communications. The devices can be used in biomedical applications, space exploration and national security applications, where its small size and telemetry abilities can allow them to be placed at different locations (e.g., near an area targeted for radiotherapy, near a security checkpoint, or in an array for use in detecting extraterrestrial radiation).

Figure 1:
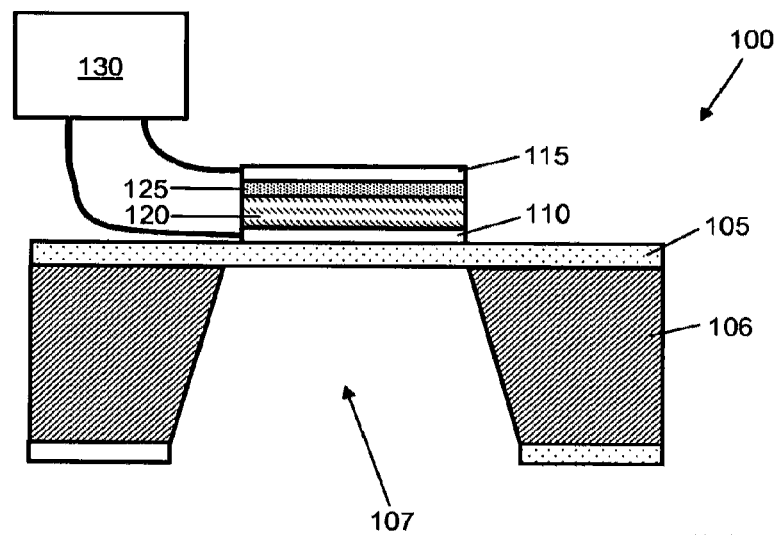
FIG. 1 is a schematic cross-sectional view of a film bulk acoustic wave resonator suitable for use according to certain embodiments of the invention.

In certain aspects of the invention, methods described herein include determining the dose of high energy radiation using the resonant frequency of the film bulk acoustic wave resonator. The dose can be determined, for example, as an actual dose (e.g., total collected energy). Alternatively, the dose can be reported as to whether it meets some threshold level. The dose can alternatively or also be determined as some other value correlated with dose (e.g., instantaneous power). As used herein, the term "determining the dose of high energy radiation" includes the determination of any value or property correlated with actual dosage, regardless of whether a numerical value of dosage is actually determined One embodiment of a film bulk acoustic wave resonator suitable for use is shown in schematic cross-sectional view in FIG. 1. Gamma radiation incident on the active area of the device (i.e., the zinc oxide layer) will reduce the resonant frequency. Film bulk acoustic wave resonator 100 includes a diaphragm layer 105, suspended above a void space 107. The diaphragm layer can, for example, be suspended by a substrate 106, as shown in the embodiment of FIG. 1. A first electrode layer 110 is disposed on the diaphragm layer 105, and a zinc oxide piezoelectric layer 120 is disposed on the first electrode 110. A second electrode layer 115 is disposed on the zinc oxide piezoelectric layer 120. In this embodiment, a layer of dielectric material (in this embodiment, silicon nitride) 125 is disposed in substantial contact with the zinc oxide piezoelectric layer, between the two electrode layers. A resonant frequency measuring circuit 130 is operatively coupled to the first electrode 110 and the second electrode 115. While in the embodiment of FIG. 1, the zinc oxide piezoelectric layer is shown as being in contact with the electrodes, the person of skill in the art will recognize that other layers (e.g., dielectric layers) can be disposed between the electrodes, between the first electrode and the diaphragm layer, and/or on the second electrode.

A device according to FIG. 1 is fabricated as follows: A bare silicon wafer is initially deposited with (low-stress) low pressure chemical vapor deposition-deposited silicon nitride on all sides. The backside silicon nitride is patterned using reactive ion etching. The wafer is then placed in a potassium hydroxide solution, in order to etch the exposed silicon completely to the topside silicon nitride. This step is followed by topside chrome/gold deposition and patterning to form the bottom electrode (i.e., the first electrode layer). Next, zinc oxide, followed by plasma-enhanced chemical vapor deposition-deposited silicon nitride are deposited on top of the structure, and patterned to expose the bottom electrode. The PECVD processing can be performed, for example, at a temperature below about 500° C. (e.g., at about 300° C.). The zinc oxide can be patterned before the PECVD silicon nitride is deposited; or it can be patterned using the PECVD silicon nitride as a mask. Finally, chrome/gold is deposited on top of the PECVD-deposited silicon nitride and patterned via liftoff to form the top electrode (i.e., the second electrode layer).

Examples of thicknesses for the various layers in this embodiment include:
 diaphragm layer: 0.1-2.0 µm thick;
 first electrode layer: 0.05-1.0 µm thick;
 dielectric layer 0.05-2.0 µm thick;
 zinc oxide piezoelectric layer: 0.1-5.0 µm thick; and/or
 second electrode layer: 0.05-1.0 µm thick.

Figure 2:
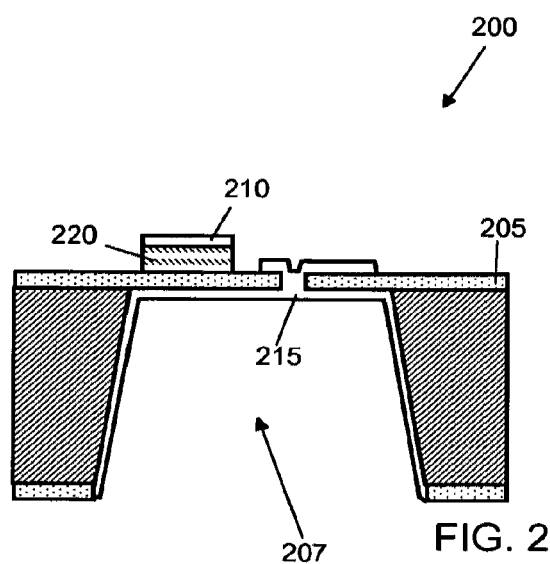
FIG. 2 is a schematic cross-sectional view of another film bulk acoustic wave resonator suitable for use according to certain embodiments of the invention.

Another embodiment of a film bulk acoustic wave resonator suitable for use is shown in schematic cross-sectional view in FIG. 2. Film acoustic wave resonator 200 includes a diaphragm layer 205, suspended above a void space 207, and having a first side and a second side. A zinc oxide piezoelectric layer 220 is disposed on the first side of the diaphragm layer, and a first electrode layer 210 is disposed on the zinc oxide piezoelectric layer 220. A second electrode layer 215 is disposed on the second side of the diaphragm layer, such that the diaphragm layer and the zinc oxide piezoelectric layer are both disposed between the first and second electrodes. A resonant frequency measuring circuit (not shown) is operatively coupled to the first electrode layer and the second electrode layer.

Examples of thicknesses for the various layers in this embodiment include:
 diaphragm layer: up to 2.0 µm thick (e.g., 0.05-1.5 µm thick);
 zinc oxide piezoelectric layer: 0.2-5.0 µm thick;
 first electrode layer: 0.05-1.0 µm thick; and
 second electrode layer: 0.05-0.2 µm thick.

Figure 3:
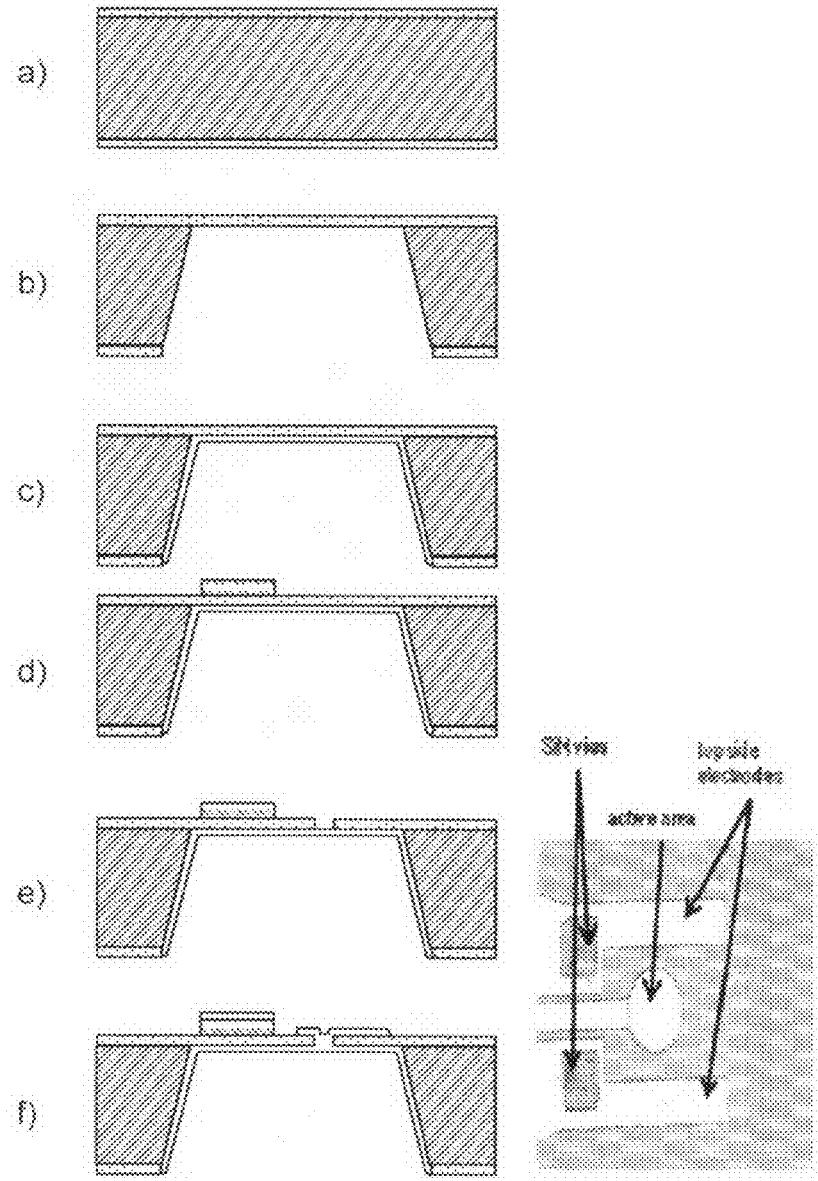
FIG. 3 is a schematic depiction of a process for making the film bulk acoustic wave resonator of FIG. 2, and a photomicrograph of the resonator so made.

The fabrication process flow for the device of FIG. 2 is shown in FIG. 3, along with a photomicrograph of the device so made. First, (a) low-stress silicon-rich silicon nitride is deposited using low pressure chemical vapor deposition at a temperature about 800° C. (0.3 µm) on the silicon wafer. Then, (b) the backside silicon nitride is patterned with reactive ion etching (RIE) and the silicon is anisotropically etched through with potassium hydroxide to form the silicon nitride diaphragm. Next, (c) layers of chromium and gold are deposited (0.01 µm /0.1 µm) onto the backside. On the top side (d) the piezoelectric semiconductor material, zinc oxide (ZnO), is sputter-deposited (0.62 µm) and patterned on the silicon nitride diaphragm. This step is followed by (e) RIE etching of vias through the silicon nitride, exposing the backside metal. Finally, (f) chromium and gold are deposited (0.01 µm/0.1 µm) and patterned on the topside, providing a topside connection to the backside metal.

Figure 4:
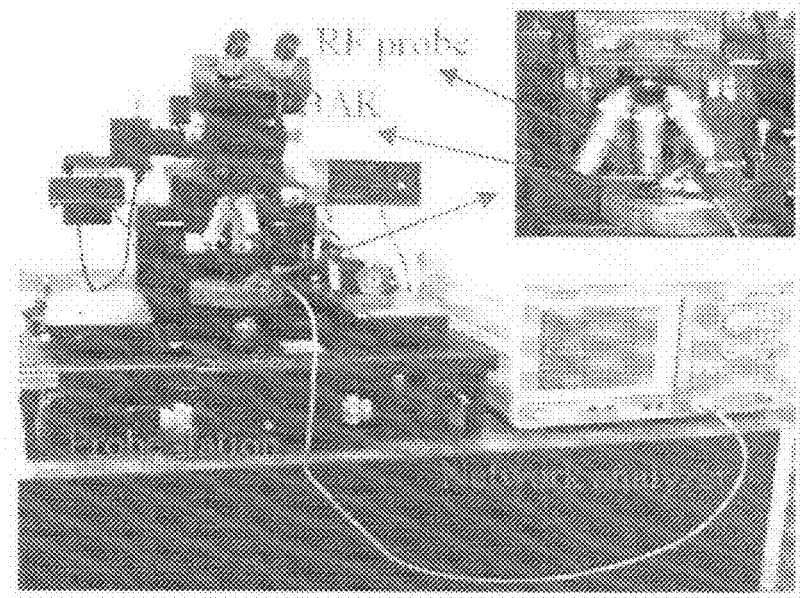
FIG. 4 is a picture of the experimental setup used in the experiments described herein.
Figure 5:
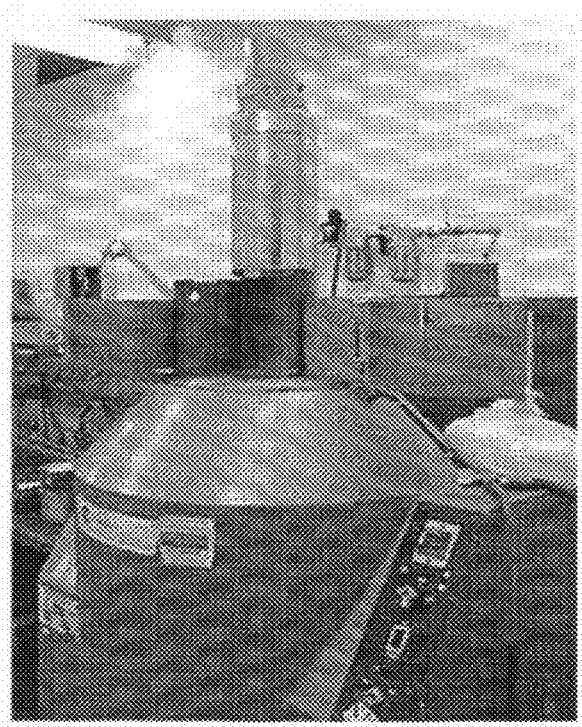
FIG. 5 is a picture of the $^{60}$Co source used in the experiments described herein.

The experimental setup for the FBAR is shown in FIGS. 4 and 5. The FBAR was irradiated by a $^{60}$Co source releasing ~1.2 MeV photons with a dose rate of 917 rad/min. The device was dosed to 20 krad, 100 krad and 200 krad, with immediate characterization between exposures. Five hours after the final exposure and characterization, the device was re-examined and was found to maintain the same resonant frequency previously measured.

Figure 6:
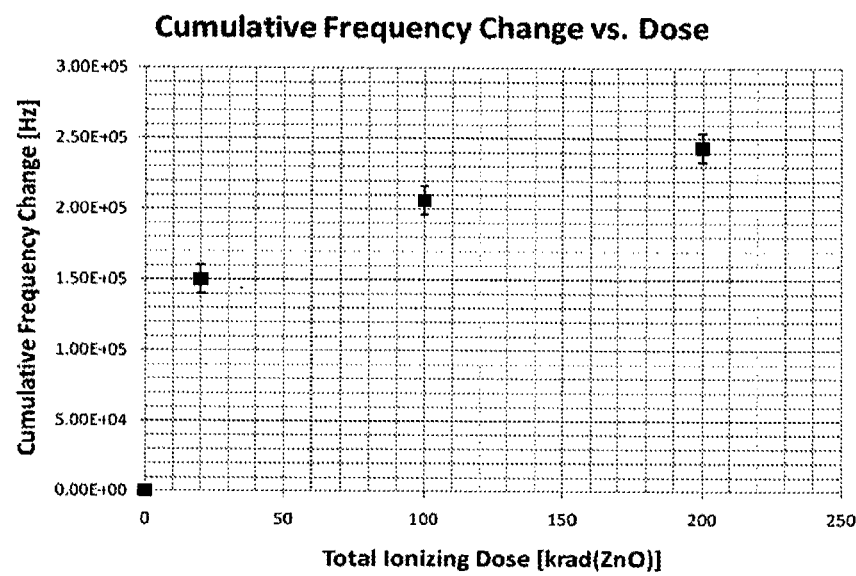
FIG. 6 is a graph of dose vs. cumulative frequency shift as measured in the experiments described herein.

The results for a typical FBAR device are shown in FIG. 6. After the first dose, the average frequency downshift of the tested devices had a sensitivity of 9.3 kHz/krad. The average sensitivity of the FBARs decreased at higher levels of radiation, 0.7 kHz/krad at 100 krad dosage and 0.6 kHz/krad at 200 krad dosage. These results show that this FBAR is sensitive to high energy gamma radiation and can be used for detection of a dose of about 220 rad.

Without intending to be bound by theory, the inventors surmise that high energy radiation incident on the dielectric layer (here, silicon nitride) and zinc oxide initiates ionization damage when electron-hole pairs (EHPs) are generated. The density of the electron-hole pairs is proportional to the energy transferred [14]. Soon after generation, a fraction of the electrons and holes recombine. Due to their higher mobility, electrons tend to recombine more quickly than holes, allowing the excess holes to migrate to either deep hole traps in the silicon nitride or traps at the silicon nitride/zinc oxide interface. Hole transport is characterized by charge "hopping" between shallow defect sites in the dielectric. Here, the trapped charge is accumulated, changing the surface potential of the semiconductor/dielectric [15], increasing the plate capacitance ($C_0$), which in turn, decreases the resonant frequency.

The radiation effects in solid state materials can be modeled [16]. The number of EHPs generated (called the generation constant), $g_0$, in the target material per unit volume per dose from an ionizing photon, is given by:

$$g_0 \left[ \frac{\#ehp}{cm^3 \cdot rad} \right] = \quad (1)$$

$$100 \left[ \frac{erg}{g} \right] \left[ \frac{1}{rad} \right] \cdot \frac{1}{1.6 \times 10^{-12}} \left[ \frac{eV}{erg} \right] \cdot \frac{1}{E_p} \left[ \frac{\#ehp}{eV} \right] \cdot \rho \left[ \frac{g}{cm^3} \right]$$

where $E_p$ is the mean free energy needed to ionize (~2× the bandgap) and $\rho$ is the density of the target material. At any given time, the fraction of holes that escape the recombination process can be represented in one dimension (x-direction) by the hole continuity equation:

$$\frac{\partial p}{\partial t} = \frac{\partial f_{p,x}}{\partial x} + G_p - R_p \quad (2)$$

where p is the hole concentration ($cm^{-3}$), $f_{p,x}$ is the hole flux, $G_p$ is the hole generation rate ($cm^{-3} s^{-1}$), and $R_p$ is the delayed hole recombination rate ($cm^{-3} s^{-1}$) [17]. If it is assumed that the device is in steady state and that the delayed recombination rate is negligible, (2) becomes:

$$\frac{\partial f_{px}}{\partial x} = G_p \quad (3)$$

where the radiation-induced hole generation rate is given by:

$$G_p = \dot{D} g_0 f_y(|E_x|) \quad (4)$$

where $\dot{D}$ is the radiation dose rate, $g_0$ is the generation constant given in (1), and $f_y$ is the charge yield which is related to the local electric field in the device which can be approximated by:

$$f_y(\vec{E}) \sim \left( \frac{|\vec{E}|}{|\vec{E} + E_0|} \right) \quad (5)$$

where $E_0$ is the threshold field constant. Integrating (3) and using boundary conditions, the hole flux can be solved for the two different electric field directions:

$$|f_{p,x}(x)| = G_p \cdot x \quad E_x > 0$$

$$|f_{p,x}(x)| = G_p \cdot (t_d - x) \quad E_a < 0 \quad (6)$$

where $t_d$ is the dielectric thickness. Finally, the rate of hole trapping near the dielectric-semiconductor interface can be expressed as:

$$\frac{dn_{ot}(x)}{dt} = (n_t(x) - n_{ot}(x)) \cdot \sigma_p \cdot |f_{p,x}(x)| - R_{n_{ot}} \quad (7)$$

where $n_{ot}$ and $n_t$ are the trapped hole density and trapped site density, respectively, and $\sigma_p$ is the hole capture cross-section ($cm^2$). The recombination factor, $R_{n_{ot}}$, represents the removal rate of trapped holes from the system. Because the re-characterization five hours after the final irradiation showed no deviation from the previous measurement, the recombination factor may be assumed to be negligible.

The FBAR can be characterized using a modified Butterworth-Van Dyke (mBVD) model. Following the methods outlined in [13], the mBVD equivalent circuit parameters can be extracted from measured data with the network analyzer.

Figure 7:
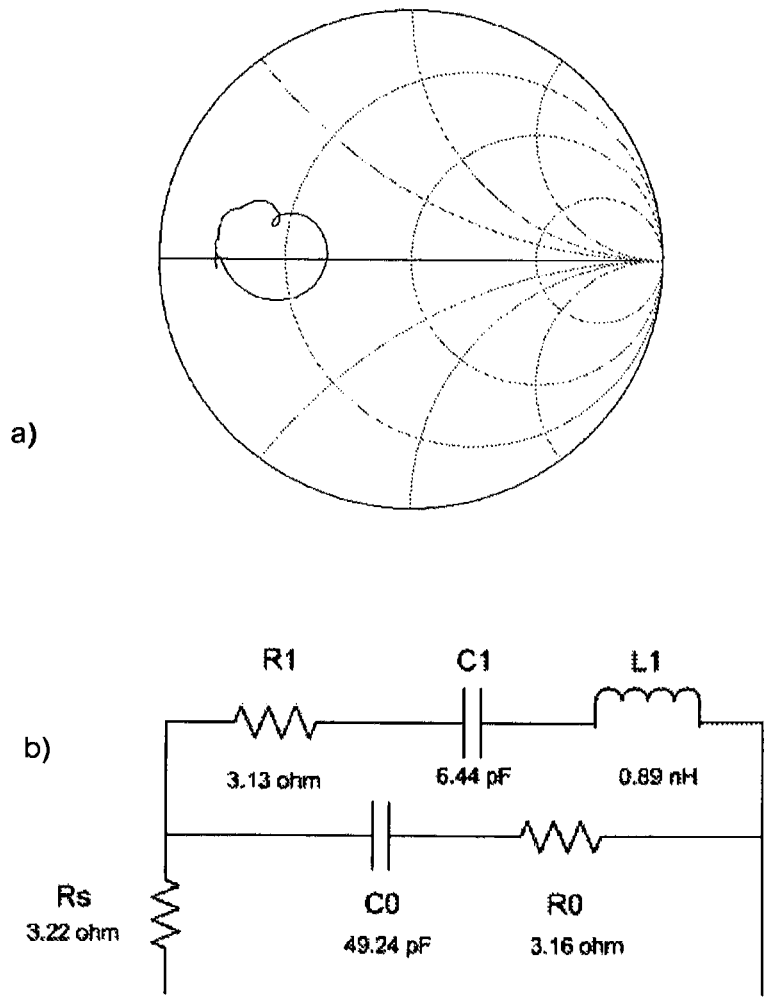
FIG. 7 provides (a) a Smith chart with frequencies from 2.0-2.4 GHz and (b) a diagram of the mBVD circuit model used in the characterization of an FBAR described herein using the modified Butterworth-Van Dyke model.

FIG. 7(a) is a Smith chart with frequencies from 2.0-2.4 GHz. FIG. 7(b) is a diagram of the mBVD equivalent circuit model used to represent the FBAR. The extracted values from the FBAR before first exposure are provided.

Figure 8:
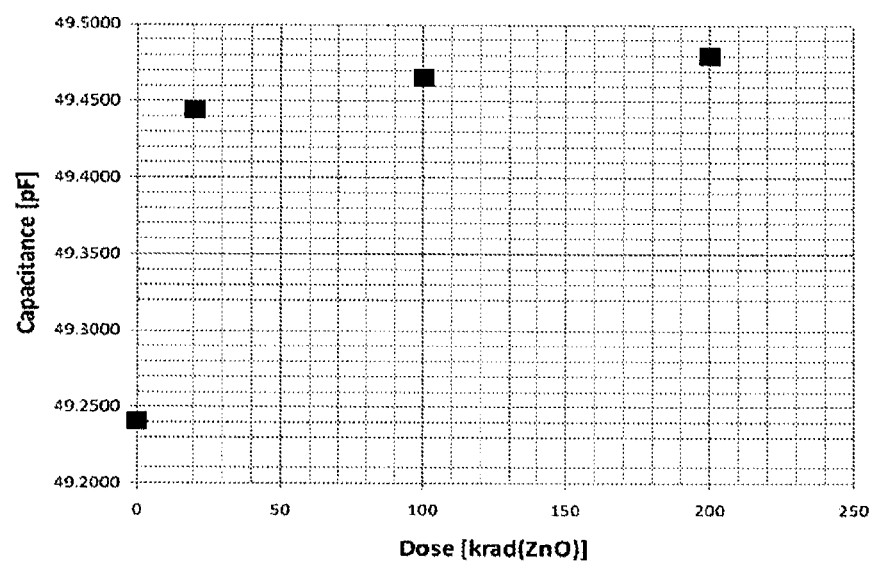
FIG. 8 is a diagram showing the analytically-determined plate capacitance of an FBAR described herein after exposure.

FIG. 8 is a diagram showing the analytically-determined plate capacitance (C0) change of the FBAR after each radiation exposure. Analytically, the reduction in the parallel resonant frequency of the FBAR indicated the increase in capacitance. After the first dose, the $C_0$ increases 0.41%, from 49.24 pF to 49.44 pF. The largest change in capacitance occurs after the first dose; subsequent irradiations showed a much smaller capacitance increase.

Figure 9:
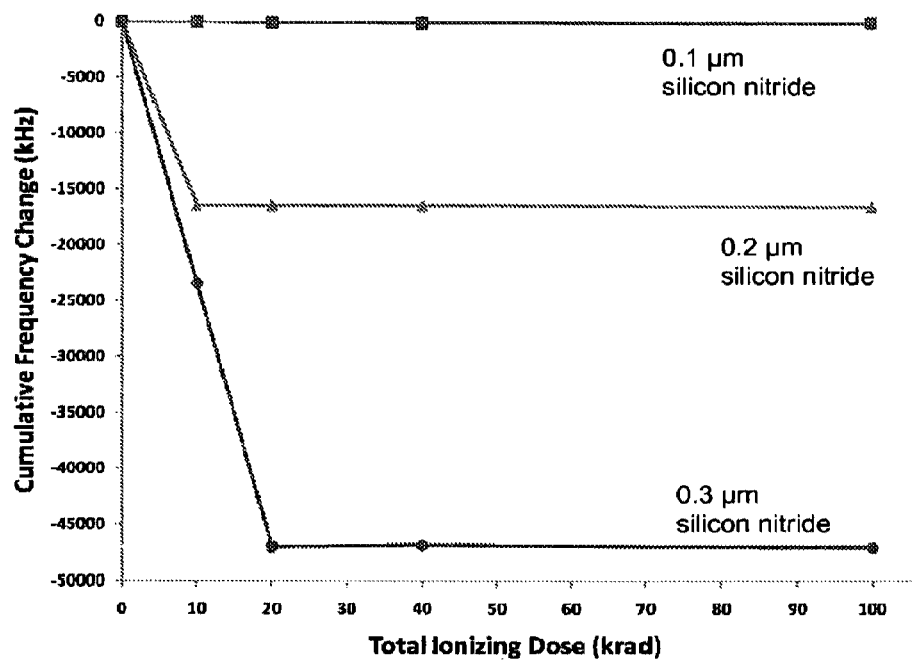
FIG. 9 is a graph of dose vs. cumulative frequency shift as measured for the devices of FIG. 1.

The devices of FIG. 1 were tested; the results are provided in FIG. 9. Varying thicknesses of PECVD-deposited silicon nitride were used as the dielectric layer in the resonator structure. Also fabricated were devices which did not have a PECVD-deposited silicon nitride layer. The devices without a PECVD-deposited silicon nitride layer, and with a 0.1 μm PECVD-deposited silicon nitride layer exhibited only a slight frequency decrease. However, the devices with 0.2 μm PECVD-deposited silicon nitride demonstrated a significant improvement; they had a sensitivity of ~1600 kHz/krad and were saturated after 10 krad. Finally, the devices with 0.3 μm PECVD-deposited silicon nitride demonstrated the best sensitivity of ~2300 kHz/krad, which is ~250 times more sensitive than the device in FIG. 2. With the noise floor of 2 kHz, the minimum detectable dose is roughly 0.87 rad. This device became saturated after the second dose (20 krad), due to a higher number of traps than 0.2 μm SiN. Since the 0.3 μm PECVD-deposited silicon nitride device was not saturated after the first dose, the maximum sensitivity using this fabrication process may have been achieved, however, increasing the silicon nitride thickness should allow for a significantly higher dynamic range. The frequency shift remained after irradiation, indicating the response is permanent. This distinguishes this sensing function with other film bulk acoustic wave resonator sensing applications, which can allow for the cancellation of response due to environmental interferents.

The following references are hereby incorporated herein by reference in their entireties.

[1] S. Stanic et al., "Radiation monitoring in Mrad range using radiation-sensing field-effect transistors," Nuc. Inst. Meth. In Phys. Res., vol. 545, pp. 252-260, 2005.

[2] J. L. Jones, et al., "Detection of shielded nuclear material in a cargo container," Nuc. Inst. and Methods In Phys. Res. A, vol. 562, pp. 1085-1088, 2006.

[3] A. Lyudin, "Study of global galactic distribution of classical novae by their gamma-ray line emission at 1.275 MeV", Nuc. Phys. A, vol. 718, pp. 413-415, 2003.

[4] R. D. Black, C. W. Scarantino, G. G. Mann, M. S. Anscher, R. D. Ornitz, and B. E. Nelms, "An analysis of an implantable dosimeter system for external beam therapy," Int. J. Rad. Onc. Bio. Phys., vol. 63, pp. 290-300, 2005.

[5] M. Takeyasu, T. Iida, T. Tsujimoto, K. Yamasaki, and Y. Ogawa., "Concentrations and their ratio of $^{222}$Rn decay products in rainwater measured by gamma-ray spectrometry using a low-background Ge detector", J. Environ. Radioact., vol. 88, pp. 74-89, 2006.

[6] F. M. Khan, The Physics of Radiation Therapy, 2nd ed. Baltimore, Md.: Williams & Wilkins, 1994.

[7] G. Beyer, G. Mann, J. Pursley, E. Espenhahn, C. Fraisse, D. Godfrey, M. Oldham, T. Carrea, N. Bolick, C. Scarantino, "An implantable MOSFET dosimeter for the measurement of radiation dose in tissue during cancer therapy," IEEE Sensors Journal, vol. 8, pp. 38-51, 2008.

[8] C. Son and B. Ziaie, "A micromachined electret-based transponder for in situ radiation measurement," IEEE Elec. Dev. Let., vol. 27, pp. 884-886, 2006.

[9] C. Son and B. Ziaie, "A wireless implantable passive microdosimeter for radiation oncology," IEEE Trans. Biomed. Eng., vol. 55, pp. 1772-1775, June 2008.

[10] M. Ueda, M. Hara, S. Taniguchi, T. Yokoyama, T. Nishihara, K. Hashimoto and Y. Satoh, "Development of an X-band filter using air-gap-type film bulk acoustic resonators," Jpn. J. Appl. Phys., vol. 47, pp. 4007-4010, 2008.

[11] H. Zhang, and E. S. Kim, "Micromachined acoustic resonant mass sensor," J. Microelectromech. Sys., vol. 14, pp. 699-706, 2005.

[12] X. Qiu, J. Zhu, J. Oiler, C. Yu, Z. Wang, and H. Yu, "Film bulk acoustic-wave resonator based ultraviolet sensor," App. Phys. Let., vol. 94, pp. 151917, 2003.

[13] J. Larson III, P. D. Bradley, S. Wartenberg, and R. C. Ruby, "Modified Butterworth-Van Dyke circuit for FBAR resonators and automated measurement system," IEEE Ultrasonics Symposium, vol. 1, pp. 863-868, 2000.

[14] T. R. Oldham, "Analysis of damage in MOS devices in several radiation environments," IEEE Trans. Nucl. Sci., vol. NS-31, pp. 1236-1241, 1984.

[15] I. S. Esqueda, H. J. Barnaby, M. L. McLain, P. C. Adell, F. E. Mamouni, S. K. Dixit, R. D. Schrimpf, and W. Xiong., "Modeling the radiation response of fully-depleted SOI n-channels MOSFETs," IEEE Trans. Nuc. Sci., vol. 56, pp. 2247-2250, 2009.

[16] H. J. Barnaby, M. L. McLain, I. S. Esqueda, and X. J. Chen., "Modeling ionizing radiation effects in solid state materials and CMOS devices," IEEE Trans. Circ. Sys., vol. 56, pp. 1870-1883, 2009.

[17] S. N. Rashkeev, C. R. Cirba, D. M. Fleetwood, R. D. Schrimpf, S. C. Witczak, A. Michez, and S. T. Pantelides, "Physical model for enhanced interface-trap formation at low dose rates," IEEE Trans. Nucl. Sci., vol. 49, pp. 2650-2655, 2002.

Unless clearly excluded by the context, all embodiments disclosed for one aspect of the invention can be combined with embodiments disclosed for other aspects of the invention, in any suitable combination.

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A method for detecting high energy radiation, the method comprising
    providing a film bulk acoustic wave resonator having a zinc oxide piezoelectric layer in substantial contact with a dielectric layer;
    exposing the film bulk acoustic wave resonator to the high energy radiation;
    determining the resonant frequency of the film bulk acoustic wave resonator; and
    determining the dose of high energy radiation using the resonant frequency of the film bulk acoustic wave resonator.

2. The method according to claim 1, wherein the dielectric layer is formed from silicon nitride.

3. The method according to claim 2, wherein the silicon nitride layer is deposited by PECVD.

4. The method according to claim 1, wherein the zinc oxide piezoelectric layer and the dielectric layer are disposed between a first electrode layer and a second electrode layer.

5. The method according to claim 1, wherein the film bulk acoustic wave resonator comprises:
    a dielectric diaphragm layer suspended above a void space, the dielectric diaphragm layer having a first side and a second side;
    a zinc oxide piezoelectric layer disposed on the first side of the dielectric diaphragm layer;
    a first electrode layer disposed on the zinc oxide piezoelectric layer;
    a second electrode layer disposed on the second side of the dielectric diaphragm layer; and
    a resonant frequency measuring circuit operatively coupled to the first electrode layer and the second electrode layer.

6. The method according to claim 5, wherein
    the dielectric diaphragm layer has a thickness in the range of 0.05 μm to 1.5 μm;
    the zinc oxide piezoelectric layer has a thickness in the range of 0.2 μm to 4.0 μm;
    the first electrode layer has a thickness in the range of 0.05 μm to 1.0 μm; and
    the second electrode layer has a thickness in the range of 0.05 μm to 0.5 μm.

7. The method according to claim 1, wherein the film bulk acoustic wave resonator comprises:
    a first electrode layer;
    a zinc oxide piezoelectric layer disposed on first electrode layer;
    a dielectric layer disposed on and in substantial contact with the zinc oxide piezoelectric layer; and
    a second electrode layer disposed on the silicon nitride layer.

8. The method according to claim 1, wherein the zinc oxide layer is substantially crystalline, with its wurtzite C axis is substantially perpendicular to its opposed surfaces.

9. The method according to claim 1, wherein the diaphragm is formed from silicon nitride.

10. The method according to claim 1, wherein the high energy radiation has an energy in the range of 1 keV to 100 MeV.

11. The method according to claim 1, wherein the high energy radiation has an energy in the range of 0.1 MeV to 10 MeV.

12. The method according to claim 1, wherein the high energy radiation has a dose in the range of 20 rad to 1000 krad.

13. The method according to claim 1, wherein the film bulk acoustic wave resonator has a resonant frequency in the range of 0.2 GHz to 10 GHz.

14. The method according to claim 1, wherein the high energy radiation is from a $^{60}$Co source.

15. The method according to claim 1, wherein the high energy radiation is from a radiation treatment for cancer.

16. The method according to claim 1, wherein the high energy radiation is from a suspected nuclear weapon.

17. The method according to claim 1, wherein the high energy radiation is from outer space.

18. A high energy radiation detector comprising a film bulk acoustic wave resonator having a zinc oxide piezoelectric layer in substantial contact with a dielectric layer; and a circuit adapted to determine a dose of high energy radiation using a resonant frequency measured by the resonant frequency measuring circuit.

19. The high energy radiation detector according to claim 18, wherein the dielectric layer is silicon nitride, and the zinc oxide piezoelectric layer and the dielectric layer are disposed between a first electrode layer and a second electrode layer.

20. The high energy radiation detector according to claim 18, wherein the dielectric layer is deposited by PECVD.

21. The high energy radiation detector according to claim 18, wherein the film bulk acoustic wave resonator comprises:
   a dielectric diaphragm layer suspended above a void space, the dielectric diaphragm layer having a first side and a second side;
   a zinc oxide piezoelectric layer disposed on the first side of the dielectric diaphragm layer;
   a first electrode layer disposed on the zinc oxide piezoelectric layer;
   a second electrode layer disposed on the second side of the dielectric diaphragm layer; and
   a resonant frequency measuring circuit operatively coupled to the first electrode layer and the second electrode layer.

22. The high energy radiation detector according to claim 21, wherein
   the dielectric diaphragm layer has a thickness in the range of 0.05 μm to 1.5 μm;
   the zinc oxide piezoelectric layer has a thickness in the range of 0.2 μm to 4.0 μm;
   the first electrode layer has a thickness in the range of 0.05 μm to 1.0 μm; and
   the second electrode layer has a thickness in the range of 0.05 μm to 0.5 μm.

23. The high energy radiation detector according to claim 18, wherein the film bulk acoustic wave resonator comprises:
   a first electrode layer;
   a zinc oxide piezoelectric layer disposed on first electrode layer;
   a dielectric layer disposed on and in substantial contact with the zinc oxide piezoelectric layer; and
   a second electrode layer disposed on the silicon nitride layer.

24. The high energy radiation detector according to claim 23, wherein
   the diaphragm layer has a thickness in the range of 0.1 μm to 2.0 μm;
   the zinc oxide piezoelectric layer has a thickness in the range of 0.1 μm to 5.0 μm;
   the dielectric layer has a thickness in the rnage of 0.05-2.0 μm thick;
   the first electrode layer has a thickness in the range of 0.05 μm to 1.0 μm; and
   the second electrode layer has a thickness in the range of 0.05 μm to 1.0 μm.

25. The high energy radiation detector according to claim 18, wherein the zinc oxide layer is substantially crystalline, with its wurtzite C axis is substantially perpendicular to its opposed surfaces.

26. The high energy radiation detector according to claim 18, wherein the diaphragm is formed from silicon nitride.

27. The high energy radiation detector according to claim 18, wherein the resonant frequency measuring circuit is operatively coupled to a system for determining a dose of high frequency radiation.

* * * * *